(12) United States Patent
Landi et al.

(10) Patent No.: US 11,062,221 B1
(45) Date of Patent: Jul. 13, 2021

(54) EXTENSIBLE DATA STRUCTURES FOR RULE BASED SYSTEMS

(71) Applicant: CERNER INNOVATION, INC., Kansas City, KS (US)

(72) Inventors: William Landi, Devon, PA (US); Vikram Anand, Downington, PA (US)

(73) Assignee: CERNER INNOVATION, INC., Kansas City, KS (US)

( * ) Notice: Subject to any disclaimer, the term of this patent is extended or adjusted under 35 U.S.C. 154(b) by 710 days.

(21) Appl. No.: 15/187,321

(22) Filed: Jun. 20, 2016

Related U.S. Application Data

(60) Provisional application No. 62/181,600, filed on Jun. 18, 2015.

(51) Int. Cl.

| | |
|---|---|
| *G06N 5/04* | (2006.01) |
| *G05B 19/00* | (2006.01) |
| *G06F 17/18* | (2006.01) |
| *G06Q 50/24* | (2012.01) |
| *G06F 19/00* | (2018.01) |
| *G06Q 10/04* | (2012.01) |
| *G06N 20/00* | (2019.01) |
| *G06F 16/2455* | (2019.01) |

(52) U.S. Cl.
CPC .............. *G06N 5/047* (2013.01); *G05B 19/00* (2013.01); *G06F 16/24564* (2019.01); *G06F 17/18* (2013.01); *G06F 19/30* (2013.01); *G06N 20/00* (2019.01); *G06Q 10/04* (2013.01); *G06Q 50/24* (2013.01)

(58) Field of Classification Search
CPC ...... G06N 5/047; G06N 99/005; G06N 20/00; G05B 19/00; G06F 17/18; G06F 17/30507; G06F 19/30; G06F 16/24564; G06Q 10/04; G06Q 50/24
See application file for complete search history.

(56) References Cited

U.S. PATENT DOCUMENTS

| | | | |
|---|---|---|---|
| 10,019,462 B1* | 7/2018 | Brown | G06F 16/27 |
| 2011/0055137 A1* | 3/2011 | Proctor | G06F 9/547 |
| | | | 706/47 |
| 2011/0225176 A1* | 9/2011 | Siegel | G06F 19/00 |
| | | | 707/756 |
| 2012/0095300 A1* | 4/2012 | McNair | A61B 5/021 |
| | | | 600/300 |
| 2013/0066643 A1* | 3/2013 | Seward | G06Q 50/22 |
| | | | 705/2 |
| 2014/0195473 A1* | 7/2014 | Citeau | G06N 5/022 |
| | | | 706/47 |

(Continued)

OTHER PUBLICATIONS

Lephoto et al. Modeling a Rule Based System for Medical Underwriting in an Insurance Industry; Oct. 24, 2014, all pages (Year: 2014).*

*Primary Examiner* — Tamara T Kyle
*Assistant Examiner* — Lahcen Ennaji
(74) *Attorney, Agent, or Firm* — Shook, Hardy & Bacon L.L.P.

(57) ABSTRACT

A computer-implemented system, methods and computer storage media are provided for creating extensible data structures for rule based systems to improve complex event processing. An underlying individual data model is accessed and the content is translated to create singleton values to be utilized in complex event processing to improve the execution fo the complex event processing.

18 Claims, 44 Drawing Sheets

| ONE CONCEPT PER PATIENT | MULTIPLE CONCEPTS PER PATIENT | |
|---|---|---|
| ◇ PATIENT | ◇ PATIENTHEIGHT | ◇ PATIENTWEIGHT |
| ABC PATIENTID | ABC PATIENTID | ABC PATIENTID |
| 3.1 HEIGHT | 3.1 HEIGHT | 3.1 WEIGHT |
| 3.1 WEIGHT | | |

(56) References Cited

U.S. PATENT DOCUMENTS

| | | | |
|---|---|---|---|
| 2015/0019248 A1* | 1/2015 | Anand | G06F 17/28 |
| | | | 705/2 |
| 2015/0347914 A1* | 12/2015 | Kwon | G06N 5/047 |
| | | | 706/48 |
| 2016/0267230 A1* | 9/2016 | Ochs | G06F 19/328 |

* cited by examiner

| ONE CONCEPT PER PATIENT | MULTIPLE CONCEPTS PER PATIENT |
|---|---|
| ```
rule Rules.BMI_OnceConcept {
    attribute {
        priority = 6;
        forwardChain = true;
    }
    declare {
        Concepts.Patient p;
    }
    when {
        (p.weight/(p.height*p.height))>=30;
    }
    then {
        System.debugOut("Contact "
            + ph.PatientId
            +" about weight management");
    }
}
``` | ```
rule Rules.BMI_MultipleConcepts {
    attribute {
        priority = 6;
        forwardChain = true;
    }
    declare {
        Concepts.PatientHeight ph;
        Concepts.PatientWeight pw;
    }
    when {
        (pw.weight/(ph.height*p.height))>=30;
        pw.PatientId==ph.PatientId;
    }
    then {
        System.debugOut("Contact "
            + ph.PatientId
            +" about weight management");
    }
}
``` |

*FIG. 3.*

|  | ONE CONCEPT PER PATIENT | MULTIPLE CONCEPTS PER PATIENT |
|---|---|---|
| EVALUATE FOR ONE (NEWLY TRUE) CONCEPT | $O(1)$ | $O(N_P)$ |
| EVALUATE FOR EVERY PATIENT | $O(N_P)$ | $O(N_P^2)$ |
| GENERALIZED: EVALUATE FOR ONE (NEWLY TRUE) CONCEPT | $O(1)$ | $O(N_P^{(N_C-1)})$ |
| GENERALIZED: EVALUATE FOR EVERY PATIENT | $O(N_P)$ | $O(N_P^{(N_C)})$ |

$N_P$: NUMBER OF PATIENTS
$N_C$: NUMBER OF CONCEPTS USED IN THE RULE (IN THE DECLARE)

*FIG. 4.*

```
rule Rules.ObeseByBMI {
    attribute {
        priority = 6;
        forwardChain = true;
    }
    declare {
        Concepts.Patient p;
    }
    when {
        p.height_m != null && p.weight_kg != null
        && (p.weight_kg.observationValue /
            ( p.height_m.observationValue * p.height_m.observationValue) >= 30);
    }
    then {
        System.debugOut("++++++++++++ Contact "+p@extId+" about weight management."
            +"Their BMI is "+(p.weight_kg.observationValue /
            ( p.height_m.observationValue *
              p.height_m.observationValue)));
    }
}
```

*FIG. 6.*

```
rule Rules.CreatePatient {
    attribute {
        priority = 2;
        forwardChain = true;
    }
    declare {
        Events.NewPatientData pd;
    }
    when {
    }
    then {
        Concepts.Patient patient = Instance.getByExtId(pd.PatientId);
        if (patient == null) {
            patient = Concepts.Patient.Patient(pd.PatientId,null,null);
        }
    }
}
```

*FIG. 8.*

```
rule Rules.SingletonValue.BodyWeightKG {
    attribute {
        priority = 5;
        forwardChain = true;
    }
    declare {
        Events.ObservationResultEvent orEvent;
    }
    when {
        orEvent.observationFocus == "LOINC | 29463-7" ||
        orEvent.observationFocus == "LOINC | 3141-9" ||
        orEvent.observationFocus == "LOINC | 8350-1" ||
        orEvent.observationFocus == "LOINC | 8351-9" ||
        orEvent.observationFocus == "LOINC | 3142-7";
        orEvent.observationValueCode == "kg";
    }
    then {
        Concepts.Patient patient = Instance.getByExtId(orEvent.PatientId);
        // patient cannot be null since a higher priority rule will create if it the
        // patient does not exist.
        DateTime eventTime = toDate(orEvent.eventTimeAsString);
        if (patient.weight_kg == null) {
            patient.weight_kg = createObsRes(orEvent,"MostRecentBodyWeightKG_");
```

FIG. 9.

```
} else if (patient.weight_kg.observationEventTime < evenTime) {
    copyObsRes(orEvent,patient.weight_kg);
  }
 }
}
```

FIG. 10.

```
rule Rules.SingletonValue.BodyHeightM {
    attribute {
        priority = 5;
        forwardChain = true;
    }
    declare {
        Events.ObservationResultEvent orEvent;
    }
    when {
        orEvent.observationFocus == "LOINC | 8302-2" ||
        orEvent.observationFocus == "LOINC | 8306-3" ||
        orEvent.observationFocus == "LOINC | 8307-1" ||
        orEvent.observationFocus == "LOINC | 8308-9" ||
        orEvent.observationFocus == "LOINC | 8301-4" ||
        orEvent.observationFocus == "LOINC | 8317-7" ||
        orEvent.observationFocus == "LOINC | 3318-5";
        orEvent.observationValueCode == "m";
        . . .
    }
}
```

FIG. 11.

```
    then {
        Concepts.Patient patient = Instance.getByExtId(orEvent.PatientId);
        // patient cannot be null since a higher priority rule will create if it the
        // patient does not exist.
        DateTime eventTime = toDate(orEvent.eventTimeAsString);
        if (patient.height_m == null) {
            patient.height_m = createObsRes(orEvent,"MostRecentBodyHeightM_");
        } else if (patient.height_m.observationEventTime < eventTime) {
            copyObsRes(orEvent,patient.height_m);
        }
    }
}
```

*FIG. 11.*
CONTINUED

```
/**
 * Let "res" be what was returned by this function.
 * If res>=0 then that is the position in the fields array.
 * If res < 0 then the fieldName is not in the array. If you want to insert it
 * then it goes at -res-1 in sortOrder (meaning after insertion that is where it
 * will be)
 */
int rulefunction RuleFunctions.DynFields._lookupFieldPos {
    attribute {
        validity = CONDITION;
    }
    scope {
        String fieldName;
        Concepts.DynFields.FieldArray list;
    }
```
. . .

*FIG. 14.*

```
body {
    // binary search
    int lb = 0;
    int up = list.fields@length-1;
    int insAt = 0;
    while (lb <= ub) {
        int mid = (lb + ub) /2;
        String curType = list.fields[list.sortOrder[mid]].name;
        int cmp= String.compareTo(curType, fieldName);
        if (cmp==0) { // curType == typeName
            return mid;
        }
        if (cmp < 0) { // curType < typeName
            lb=mid+1;
            insAt=ub+1;
        } else { // curType > typeName
            ub=mid-1;
            insAt=1b
        }
    }
    return -(insAt+1);
}
```

```
Int rulefunction RuleFunctions.DynFields._lookupFieldPosDecode {
attribute {
    validity = CONDITION;
}
scope {
    int fieldPosResult;
}
body {
    if (fieldPosResult < 0) {
        return -fieldPosResult – 1;
    }
    // or do we want this to be an error
    return fieldPosResult;
}
}
```

*FIG. 15.*

```
Concepts.DynFields.Field rulefunction RuleFunctions.DynFields._lookupField {
    attribute {
        validity = CONDITION;
    }
    scope {
        String fieldName;
        Concepts.DynFields.FieldArray list;
    }
    body {
        int at = _lookupFieldPos (fieldName,list);
        if (at < 0) return null;
        return list.fields[list.sortOrder[at] ];
    }
}
```

*FIG. 16.*

```
Concepts.DynFields.Field rulefunction RuleFunctions.DynFields.DynFields._lookupAndInsertField {
    attribute {
        validity = ACTION;
    }
    scope {
        Concepts.DynFields.FieldArray fa;
        String fieldName;
        String type;
    }
    body {
        int lookupRes = _lookupFieldPos (fieldName,fa);
        if (lookupRes >=0) {
            //this should not be called, but if it is, already there so don't need to do anything
        } else {
            int realPos = fa.sortOrder@length;
            fa.fields[realPos]=
                Concepts.DynFields.Field.Field(_getFieldExtIdPre(fieldName),realPos,fieldName,type);
            int addAt = _lookupFieldPosDecod(lookupRes);
            for (int at = fa.sortOrder@length; at>addAt; at--) {
                fa.sortOrder[at]=fa.sortOrder[at-1];
            }
            Concepts.DynFields.Field field=fa.fields[fa.sortOrder[lookupRes]];
            return field;
        }
    }
}
```

*FIG. 17.*

| # OF FIELDS ADDED | MAX (ms) | TOTAL (SECONDS) | AVG (ms) |
|---|---|---|---|
| 500 | 1 | 0.12 | 0.23 |
| 5,000 | 4 | 1.1 | 0.23 |
| 50,000 | 117 | 90.1 | 1.80 |

*FIG. 18.*

```
Concepts.vMRObservationResult rulefunction RuleFunctions.DynFieldsGlob.getObsResDG {
    attribute {
        validity = CONDITION;
    }
    scope {
        Concepts.Patient p;
        String fieldName;
        Concepts.DynFieldMetaData md;
    }
    body {
        Concepts.DynFields.FieldArray fields=md.obsResFields;
        Concepts.DynFields.Field f = _lookupField(fieldName, fields);
        if (f == null || f.pos <= p.dynObsRes@length) {
            return null;
        }
        return p.dynObsRes[f.pos];
    }
}
```

FIG. 19.

```
void rulefunction RuleFunctions.DynFieldsGlob.setObsReDG {
  attribute {
    validity = ACTION
  }
  scope {
    Concepts.Patient p;
    String fieldName;
    Events.ObservationResultEvent val;
    Concepts.DynFields.FieldMetaData md;
  }
  body {
    Concepts.DynFields.Field
Field=_lookupAndInsertField(md.obsResFields,fieldName,PE_Config.tObsRes);
    while (p.dynObsRes@length <= field.pos) {
      p.dynObsRes[p.dynObsRes@length]=null;
    }
    if
(p.dynObsRes[field.pos]=createObsRes(val,_getFieldExtIdPre(fieldName)+"_"+val.PatientI
d);
    } else {
      copyObsRes(val,p.dynObsRes[field.pos]};
    }
  }
}
```

FIG. 20.

```
rule Rules.DynFieldsGlob.DG_ObeseByBMI {
    attribute {
        priority = 6;
        forwardChain = true;
    }
    declare {
        Concepts.Patient p;
        Concepts.DynFields.FieldMetaData fmd_singleton;
    }
    when {
        getObsResDG(p,"height_m",fmd_singleton) != null &&
        getObsResDG(p,"weight_kg",fmd_singleton) !=null &&
        (getObsResDG(p,"weightkg",fmd_singleton).observationValue /
         ( getObsResDG(p,"height_m",fmd_singleton).observationValue *
           getObsResDG(p,"height_m",fmd_singleton).observationValue) >=30);
    }
    then {
        System.debugOut(Contact "+p@extId+" about weight management.);
    }
}
```

FIG. 21.

| FUNCTION | Worse case complexity | Expected complexity |
|---|---|---|
| _getFieldExtIdPre | $O(1)$ | $O(1)$ |
| _lookupAndInsertField | $O(N_f)$ | $O(\log(N_f))^6$ |
| _lookupField | $O(\log(N_f))$ | $O(\log(N_f))$ |
| _lookupFieldPos | $O(\log(N_f))$ | $O(\log(N_f))$ |
| _lookupFieldPosDecode | $O(1)$ | $O(1)$ |
| getObsResDG | $O(\log(N_f))$ | $O(\log(N_f))$ |
| setObsResDG | $O(N_f)$ | $O(\log(N_f))$ [see footnote for _lookupAndInsertField] |

$N_c$: Number of Concepts used in the rule (in the declare)
$N_f$: The number of unique dynamic fields that exist.
$N_p$: Number of patients

*FIG. 22.*

|  | Singleton FieldMetaData | Each patient maintains its own FieldMetaData |
|---|---|---|
| Pros | - Storage of FieldMetaData once<br>- Worst case complexity of "set" function is clearly better than the "each patient" case. | - If for a significant number of patients the number of fields used in the patient is significantly less than the number of fields used in all patients, the space usage for storing values will be much less and the effective $N_f$ in complexity analysis will be much smaller |
| Cons | - Need to have a spot in the value array for each field used anywhere even if that field is not used with that patient. | - Storage of FieldMetaData once per patient (albeit only the fields relevant to that patient)<br>- Worst case complexity of "set" function is clearly worse that singleton case but it is not clear whether in practice it is "on average" worse. |

FIG. 23.

```
declare {
    Concepts.Patient p;
}
when {
    p.weight_kg.observationValue >= 100;
}
then {...}
```

FIG. 24.

```
declare {
    Concepts.Patient p;
    Concepts.DynFields.FieldMetaData fmd_singleton;
}
when {
    getObsResDG(p,"weight_kg",fmd_singleton >= 100;
}
then {...}
```

FIG. 25.

```
rule Rules.DynFieldsGlob.DG_BodyWeightKG {
  attribute {
    priority = 5;
    forwardChain = true;
  }
  declare {
    Events.ObservationResultEvent orEvent;
    Concepts.DynFields.FieldMetaData fmd_singleton
  }
  when {
    orEvent.observationFocus == "LOINC | 29463-7" ||
    orEvent.observationFocus == "LOINC | 8141-9" ||
    orEvent.observationFocus == "LOINC | 8350-1" ||
    orEvent.observationFocus == "LOINC | 8351-9" ||
    orEvent.observationFocus == "LOINC | 3142-7";
    orEvent.observationValueCode == "kg";
  }
  then {
    String fieldName = "weight_kg";
    String fieldType = "obsRes";
    Concepts.Patient patient = Instance.getByExtId(orEvent.PatientId);
    DateTime eventTime = toDate(orEvent.eventTimeAsString);
    Concepts.vMR.ObservationResult tmp =
        getObservationResult
    if (tmp == null || tmp.observationEventTime < eventTime) {
      setObseResDG(patient,fieldName,orEvent,fmd_singleton);
    }
  }
}
```

*FIG. 27.* setObsResDG(patient,fieldName,orEvent,fmd_singleton);

FIG. 28.

```
Events.SetObservationResult setEvent =Event.createEvent("[magic string]");
Event.assertEvent(setEvent);
```

*FIG. 29.*

```
rule Rules.DynFieldsGlob.DG_UpdateFieldsObsRes {
    attribu
        priority = 3;
        forwardChain = false;
    }
    declare {
        Events.SetObservationResult e;
    }
    when {
    }
    then {
        Concepts.DynFields.FieldMetaData         fmd =
Instance.getByExtId(PE_Config.fieldMetaData_id);
        _lookupAndInsertField(fmd.obsResFields,e.fieldName,e.fieldType);
    }
}
```

FIG. 31.

```
rule Rules.DynFieldsGlob.DG_SetValueObsRes {
    attribute {
        priority = 4;
        forwardChain = true;
    }
    declare {
        Events.SetObservationResult e;
    }
    when {
    }
    then {
        Concepts.DynFields.Fields.FieldMetaData fmd=Instance.getByExtId
(PE_Config.fieldMetaData_id);
        Concepts.Patient patient = Instance.getByExtId(e.PatientId);
        setObsResDG(patient,e.fieldname,e,fmd);
        Event.consumeEvent(e); // prevents real rules from being considered
    }
}
```

*FIG. 32.*

| NUM PATINETS | STATIC FIELD TIME (MS) | DYN FIELD TIME (MS) DIRECT CALL | DYN FIELD TIME (MS) SET EVENT |
|---|---|---|---|
| 10,000 | 1 | 96 | 5 |
| 50,000 | 1 | 343 | 7 |
| 100,000 | 2 | 632 | 9 |
| 200,000 | 2 | 1,267 | 13 |

*FIG. 33.*

| | |
|---|---|
| "newly meets" | |
| if (p.edVal == null \|\| (p.edVal.dt < vo.dt) {<br>  p.edVal = vo;<br>} | |
| If one processing is more recent then use the one processing. | |
| "newly not meets": 1. Passage of Time | |
| if (p.edVal == vo) {<br>  p.edVal = null;<br>} | |
| This works under the assumption that there is one time window with no gaps when objects qualify for inclusion in the sequence. In that case, if this was the most recent but it no longer qualifies because it no longer falls into the time window, we can't know of a more recent one that does (as that contradicts that this is the most recent). | |
| "newly not meets" : 2. Data Change | |
| Query to get full sequence and compute. | |
| The only other approach is to maintain the while sequence in "p", but I would rather just query in that case. | |

*FIG. 34.*

| | |
|---|---|
| "newly meets" | if (p.edVal == null \|\| (p.edVal.v > vo.v) { p.edVal = vo; } |
| | If one processing is smaller, store it |
| "newly not meets": 1. Passage of Time | Query to get full sequence and compute. |
| | The only other approach is to maintain the while sequence in "p", but I would rather just query in that case. |
| "newly not meets": 2. Data Change | Query to get full sequence and compute. |
| | The only other approach is to maintain the while sequence in "p", but I would rather just query in that case. |

*FIG. 35.*

| | |
|---|---|
| "newly meets" | if (p.edVal == null \|\| (p.edVal.v < vo.v) {<br>  p.edVal = vo;<br>} |
| | If one processing is smaller, store it |
| "newly not meets": 1. Passage of Time | Query to get full sequence and compute. |
| | The only other approach is to maintain the while sequence in "p", but I would rather just query in that case. |
| "newly not meets": 2. Data Change | Query to get full sequence and compute. |
| | The only other approach is to maintain the while sequence in "p", but I would rather just query in that case. |

*FIG. 36.*

| | | | | | | | |
|---|---|---|---|---|---|---|---|
| "newly meets" | p.edVal++; | One more than before. | "newly not meets": 1. Passage of time | p.edVal--; | One less than before | "newly not meets": 2. Data Change | p.edVal--; | One less than before. |

*FIG. 37.*

| | |
|---|---|
| "newly meets" | p.edVal.count++; p.edVal.total+=vo.v; |
| The average is obviously p.edVal.total/p.edVal.count | |
| "newly not meets": 1. Passage of time | |
| p.edVal.count--; p.edVal.total-= vo.v; | |
| The average is obviously p.edVal.total/p.edVal.count | |
| "newly not meets": 2. Data Change | |
| p.edVal.count--; p.edVal.total-= prev(vo.v); | |
| The average is obviously p.edVal.total/p.edVal.count Prev(vo.v) is the before change value of vo.v. If that is not known then will need to query to get full sequence and compute. | |

FIG. 38.

```
"newly meets"

if (p.edVal.mostRecent == null) {
    p.edVal.mostRecent = vo;
} else {
    if (p.edVal.mostRecent.dt < vo.dt) {
        p.edVal.previous = p.edVal.mostRecent
        p.edVal.mostRecent = vo;
    } else {
        if (p.edVal.previous = vo;
    }
}
```

If one processing is more recent then use the one processing.

"newly not meets": 1. Passage of Time

```
if (p.edVal.mostRecent == vo) {
    p.edVal.mostRecent = null;
    p.edVal.previous = null; // C1
} else if (p.edVal.previous == vo) {
    p.edVal.previous = null;
}
```

| |
|---|
| ... |
| This works under the assumption that there is one time window with no gaps when objects qualify for inclusion in the sequence. In that case, if this was the most recent but it no longer qualifies because it no longer falls into the time window, we can't know of a more recent one that does (as that contradicts that this is the most recent). The assignment with the comment "c1" makes sense because if the most recent is too old the second most recent is also too old and in the rare situation they have the same (or almost same) timestamp, we cannot be sure which one will be processed firet, so there is some chance it is not null already |
| "newly not meets": 2. Data Change |
| Query to get full sequence and compute. |
| The only other approach is to maintain the while sequence in "p", but I would rather just query in that case. |

*FIG. 39.*
CONTINUED

| | |
|---|---|
| "newly meets" | |
| if (p.edVal == null \|\| (p.edVal.dt > vo.dt) { p.edVal = vo; } | If one processing is more recent thne use the one processing. |
| "newly not meets": 1. Passage of Time | Query to get full sequence and compute. |
| | The only other approach is to maintain the while sequence in "p", but I would rather just query in that case. |
| "newly not meets": 2. Data Change | Query to get full sequence and compute. |
| | The only other approach is to maintain the while sequence in "p", but I would rather just query in that case. |

*FIG. 40.*

| | |
|---|---|
| Content Translator | Content Translator: in this model content in one form (currently as XML files) is automatically converted into Pluggable Content as defined above. This can also be generalized into a content IDE (Integrated Development Environment). Generalized Analogy: Xcode IDE, Android Eclipse IDE/SDK. |
| Core Product | Core Product: may include CareXcell or Healthe Care but does not include the content itself. Analogy: Smart Phone. |
| $N_c$ | Number of Concepts used in the rule (in the declare) |
| $N_f$ | The number of unique dynamic fields that exist. |
| $N_g$ | Number of times a "get" function is called with dynamic fields. |
| $N_p$ | Number of Patients |
| $N_s$ | Number of times a "set" function is called with dynamic fields. |
| Patient Data Model | Patient Data Model: The data model for patient data assumed by the content. |
| Pluggable Content | Pluggable Content: This is the functionality related to a disease or other clinically interesting concept. It is released independently of the Core Product but can also require particular versions (possibly one version) of the Core Product to work. Analogy: Smartphone App |
| Rete Data Model | Rete Data Model: The data model for patient data used in the rules/ Rete network. In general this may or may not be the same as the Patient Data Model. In CEP, such as TIBCO DE, this manifests as "Concepts" or "Events". |

*FIG. 41.*

EXTENSIBLE DATA STRUCTURES FOR RULE BASED SYSTEMS

RELATED APPLICATIONS

This application is a non-provisional of U.S. Provisional Application Ser. No. 62/181,600 filed on Jun. 18, 2015, the entirety of which is hereby incorporated by reference herein.

BRIEF DESCRIPTION OF THE DRAWINGS

FIG. 3 is a graphical representation of an exemplary rule structure;

FIG. 4 is a graphical representation of an exemplary rule evaluation;

FIG. 6 is a graphical representation of an exemplary rule;

FIGS. 8-11 are graphical representations of exemplary rules;

FIG. 14 is a graphical representation of an exemplary negative value;

FIG. 15 is a graphical representation of an exemplary result returned;

FIG. 16 is a graphical representation of an exemplary clause of rules;

FIG. 17 is a graphical representation of an exemplary array;

FIG. 18 is a graphical representation of an exemplary total time to add fields;

FIG. 19 is a graphical representation of exemplary rule functions;

FIG. 20 is a graphical representation of example 0(1);

FIG. 21 is a graphical representation of exemplary rule reconsideration;

FIGS. 22-23 are graphical representation tables summarizing complexities;

FIG. 24 is a graphical representation of an exemplary rule;

FIG. 25 is a graphical representation of replacing a static field with a dynamic field and function call;

FIGS. 27-29 are graphical representations of exemplary dynamic rule replacement;

FIG. 31 is a graphical representation of priority rules;

FIG. 32 is a graphical representation of exemplary dynamic field values;

FIG. 33 is a graphical representation of static and dynamic fields with set events; and FIGS. 34-41 are graphical representation of exemplary function computation approaches.

DETAILED DESCRIPTION

Figure 1:
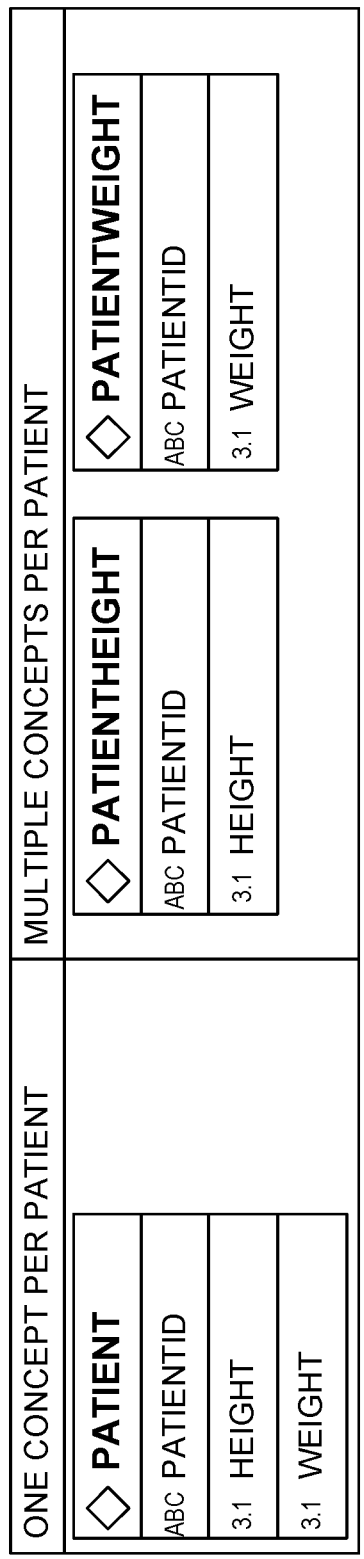
FIGS. 1-2 are graphical representations of exemplary data structures.

An approach for translating clinical content to rules evaluated with a RETE algorithm is provided. The analysis is directed to the specific context of generating complex event processing (CEP) rules, for instance for TIBCO BE, but most if not all of the fundamental complexity issues in CEP would be exist in any RETE implementation even if it was batch based and not (real time) event based. Embodiments of the present invention apply to both batch rule based solutions and event rule based solutions.

Embodiments of the present invention will apply to other content if some or all of the key assumptions are met. This analysis is about the cost of evaluating rules and not about the actions/interventions taken when conditions are true. In examples, actions/interventions are simply messages to the console. This is done to keep the examples simple.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

An exemplary computing environment suitable for use in implementing embodiments of the present invention is described below. An exemplary computing environment (e.g., medical-information computing-system environment) with which embodiments of the present invention may be implemented is provided. The computing environment is merely an example of one suitable computing environment and is not intended to suggest any limitation as to the scope of use or functionality of the invention. Neither should the computing environment be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

The computing environment comprises a computing device in the form of a control server. Exemplary components of the control server comprise a processing unit, internal system memory, and a suitable system bus for coupling various system components, including data stores, with the control server. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server typically includes therein, or has access to, a variety of non-transitory computer-readable media. Computer-readable media can be any available media that might be accessed by control server, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server might operate in a computer network using logical connections to one or more remote computers. Remote computers might be located at a variety of locations in a medical or research environment, including clinical laboratories (e.g., molecular diagnostic laboratories), hospitals and other in individual settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers might also be physically located in nontraditional medical care environments so that the entire healthcare community might be capable of integration on the network. The remote computers might be personal computers, servers, routers, network PCs, peer devices, other common network nodes, or the like and might comprise some or all of the elements described above in relation to the control server. The devices can be personal digital assistants or other like devices.

Computer networks comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server, the data store, or any of the remote computers. For example, various application programs may reside on the memory associated with any one or more of the remote computers. It will be appreciated by those of ordinary skill in the art that the network connections shown are exemplary and other means of establishing a communications link between the computers (e.g., control server and remote computers) might be utilized.

In operation, an organization might enter commands and information into the control server or convey the commands and information to the control server via one or more of the remote computers through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server. In addition to a monitor, the control server and/or remote computers might comprise other peripheral output devices, such as speakers and a printer.

Although many other internal components of the control server and the remote computers are not shown, such components and their interconnection are well known. Accordingly, additional details concerning the internal construction of the control server and the remote computers are not further disclosed herein.

The methods, systems and computer readable media, described herein, are directed to improving a technological process. As described in more detail herein, embodiments of the present invention improve the functioning of a computer itself. In particular, the extensible data structures for rule based systems described herein improve the processing time and throughput of a rules based system.

Terminology

For the purpose of this analysis, three main parts are distinguished from the content perspective.
  i. Core Product: may include CareXcell or Healthe Care but does not include the content itself. Analogy: Smart Phone.
  ii. Pluggable Content: This is the functionality related to a disease or other clinically interesting concept. It is released independently of the Core Product but can also require particular versions (possibly one version) of the Core Product to work. Analogy: Smartphone App (not implying nor excluding an app market concept).
  iii. Content Translator: In this model content in one form (currently as XML files) is automatically converted into Pluggable Content as defined above. This can also be generalized into a content IDE (Integrated Development Environment). Generalized Analogy: XCode IDE, Android Eclipse IDE/SDK.
Distinguishing between two data models:
  iv. Individual Data Model: The data model for individual medical data assumed by the content. HL7 vMR or FHIR can be used but there are many other options as well.
  v. Rete Data Model: The data model for individual data used in the rules/Rete network. In general this may or may not be the same as the Individual Medical Data Model. In CEP, such as TIBCO BE, this manifests as "Concepts" or "Events".

These are key terms used repeatedly within this document.

Key Assumptions

Assumption 1. Rules are based on variables which have zero or one values.

SingletonValueAs described below, this is an incredibly useful property. If the content does not have it, and it is possible to modify the content to adhere to this property, it is well worth considering doing that.

Assumption 2. There is an underlying Individual Data Model that is assumed by the content but not defined by it.

Changes to this model can require changes to the Core Product and Content Translator.

In Healthcare HL7 vMR and FHIR are good candidates for developed content but many others are also possible.

Assumption 3. If the language (grammar and/or semantics) of how content is received and the individual data model do not change, then Pluggable Content can be generated with the Content Translator with no change to the Core Product.

For XML based content this means if the XML Schema for Content and the subset of vMR used doesn't change, then the Pluggable Content can be released with no changes to the Content Translator or the Core Product.

The purpose of this assumption is to make it so that new content doesn't, in general, require updates to the Core Product or (less importantly) Content Translator.

Assumption 4. If the language (grammar and/or semantics) of how content is received and the individual data model do not change, then the Rete Data Model should not have to be updated.

The Rete Data Model for NFR (non-functional requirement reasons, e.g. performance) may be updated.

The purpose of this is non-functional without down time and do reprocessing in order to add new content.

Note that the underlined part of Assumption 3&4 are word for word identical.

Rete Data Structure: Cost of Multiple Concepts per Individual

For example, where each individual has a most recent height and weight and we have a rule that if their BMI is 30 or higher than a care manager contacts them about weight management.

Referring to FIG. 1, there are two fundamentally different ways to represent this in the Rete Data Structure.

Figure 2:
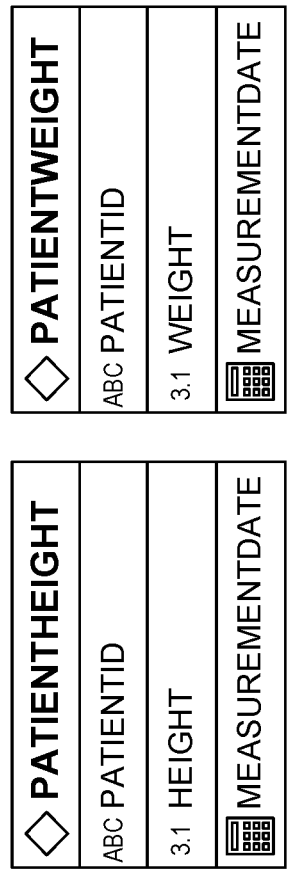

In such a simple example the "Multiple Concepts" approach is unusual but this approach does have attraction in many real scenarios. With reference to FIG. 2, even changing from storing the most recent height and weight to storing all height and weight measurements with the date of measurement, the example in FIG. 2 becomes a more realistic design. If used as the Rete Data Structure, vMR and FHIR are "Multiple Concept" approaches. The "Multiple Concept" approach is what is currently taken in the Rete Data Model in CareXcell. In the code below we are using the version without measurementDate for simplicity. It assumes height is in Meters and weight is in Kilograms.

For those who are unfamiliar with TIBCO's CEP rules but understand rules in general, the example in FIG. 3 is mostly readable. When you have multiple lines in a "when" separated by a semicolon they are "anded". So in the multiple concept rule the real condition is (pw.weight/(ph.height*ph.height))>=30 && pw.IndividualId==phIndividualId;

You could write it that way but if you do it reduces the CEP engines ability to optimize the evaluation (it forces the left of the "and" to be evaluated before the right). Priority is just used to determine the order to evaluate rules when multiple are true.

FIG. 4 is an examination of the complexity of these two options. The above example has 2 concepts used in the declare section in the "Multiple Concepts per Individual" option. Scenarios below prefixed with "Generalized:" generalize the above examples from having 2 concepts in the declare to having $N_c$ concepts in the declare. $N_p$ is the number of individuals. It is implicitly assumed every individual has both a height and a weight which is the worst case assumption (given 0 or 1 per individual).

Given that in practice we expect $N_p$ to be 100,000 plus (and potentially millions) and that we expect than 3 variables (SingletonValue), the conclusion to a design of the Rete Data Model which involves results in more than one individual concept (linked by a individual ID) in rules is untenable.[1]

[1] Theoretically, if there is a second patient concept which is very sparse (substantial majority of patients have no values), then this conclusion can be challenged, but practically the conclusion is sound.

Design Constraint 1 All individual data used within the conditions of a rule must come from one concept.[2]

[2] This implies that if you need patient data from another concept, the suggested approach is to do a query from the when clause. However, a goal of the design of the Rete Data Model should be to minimize if not eliminate cases where this is needed.

Impacts of "SingletonValue" in Content

Any realistic rules based on a realistic underlying Patent Data Model are unlikely to meet Design Constraint 1. Certainly many desirable rules (including the example below) based on HL7 vMR or FHIR would violate this constraint. However it is possible to define a concept of SingletonValue and write rules that meet this constraint. SingletonValueSingletonValue are calculations against the Individual Data Model. A key attribute of SingletonValue with the attribute that for a given individual it corresponds to either zero or one value. An Example of an SingletonValue is "Most Recent Weight". If there is no weight there is no value (zero) but otherwise there is exactly one value.

A more detailed continuation of the obesity content example is provided. This version will be based on the vMR model.

Consider a design for the Rete Data Model which has a individual concept with a field for each "SingletonValue" in the content. Given the property of SingletonValue having zero or one value and the expression of a rule is based upon SingletonValue, Assumption 1 is easy to meet. The astute reader will note that this approach is clearly violating Assumption 4. We will address Assumption 4 later but ignoring it for now allows for a cleaner presentation of the concepts involved. The key concepts can still be met when we add Assumption 4 in later.

Figure 5:
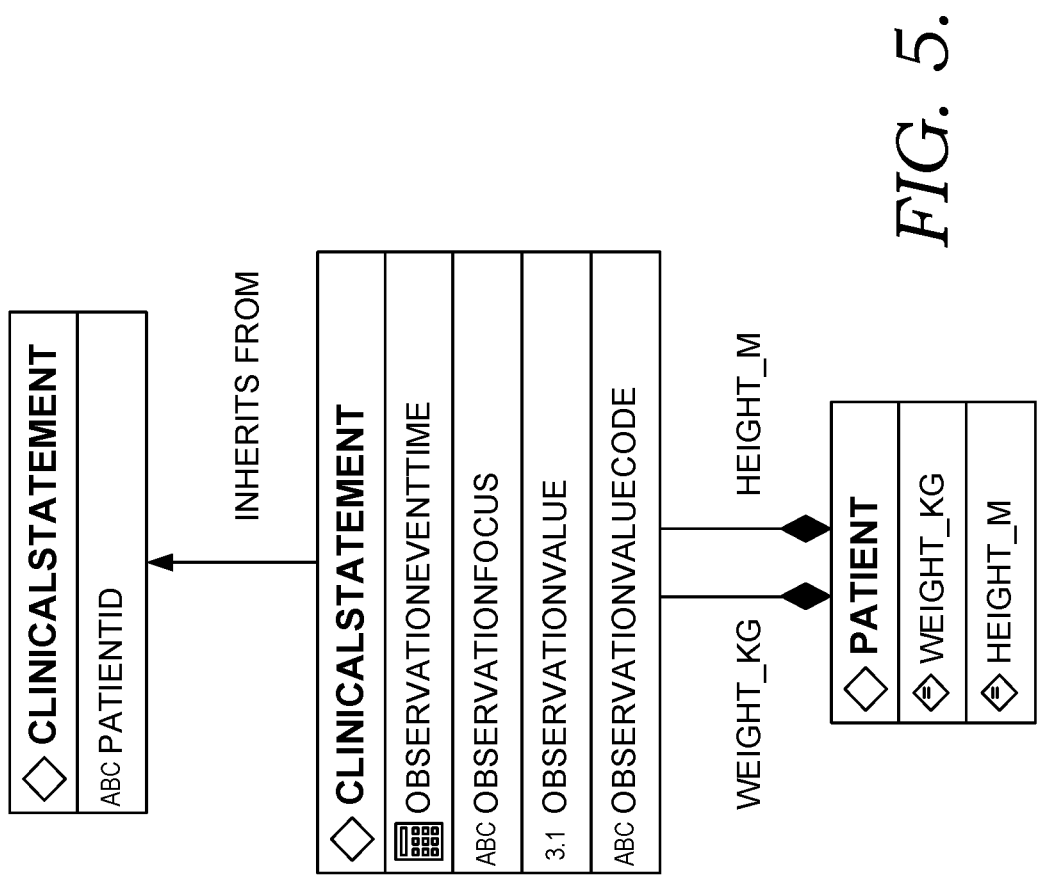
FIG. 5 is a graphical representation of an exemplary data model design.

Using this approach the concepts used for this example are shown in FIG. 5.

This Concept design has a subset of the vMR model with simplified inheritance (ClincalStatement and ObservationResult) with a non-vMR individual Concept to bind things together. Note Individual uses these concepts as "ContainedConcepts". If you use "ConceptReference" then accessing the sub-fields of those fields in the "when" clause of rules is not allowed by TIBCO BE. Using this model, the obesity rule can be written as shown in FIG. 6.

This clearly meets Design Constraint 1 and results in the desired constant, O(1), amount of work when processing a individuals height or weight. However, it still needs to be explored how to get from vMR to the SingletonValue value in a constant amount of work for a given ClinicalStatement. In this example there are two Singleton Value.

1. Weight_kg
   Returns the most recent ObservationResult (for a individual) whose observationFocus is one the values in {"LOINC|29463-7", "LOINC|3141-9", "LOINC|8350-1", "LOINC|8351-9", "LOINC|3142-7"}
2. Height_m
   Returns the most recent ObservationResult (for a individual) whose observationFocus is one the values {"LOINC|8302-2", "LOINC|8306-3", "LOINC|8307-1", "LOINC|8308-9", "LOINC|8301-4", "LOINC|3317-7", "LOINC|3318-5"}

The approach taken here is to assume there is an event that corresponds to a complete ClinicalObject in vMR. The events may be created using any variety of techniques. They can be events and not concepts as they are only used to populate values in the individual concept for Singleton Value "variables" and hence can be ephemeral. In the sample code there is an html page that creates these events for testing purposes.

Figure 7:
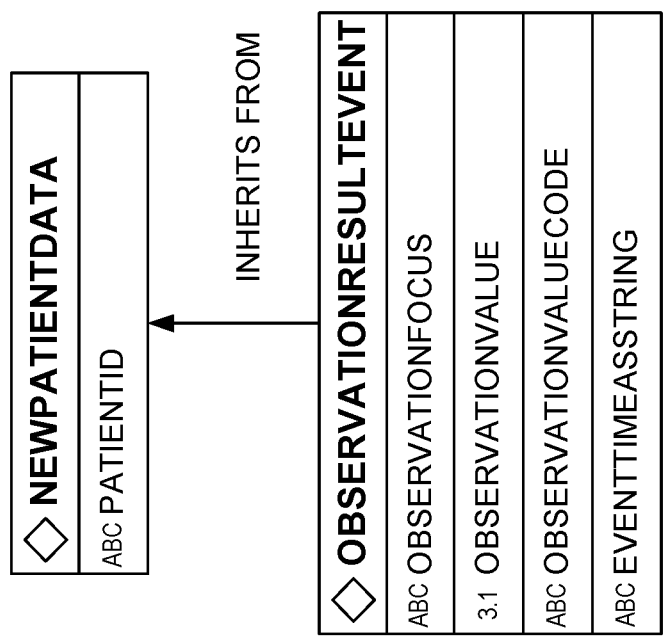
FIG. 7 is a graphical representation of an exemplary event structure.

The event structure used is shown in FIG. 7.

There is one rule for all events and a rule for each Singleton Value. The rule for all events simply creates an empty Individual Concept if none currently exists as shown in FIG. 8. The nulls are indicating that we have not processed any data yet for this individual. The rule for weight_kg is shown in FIGS. 9 and 10. This rule invokes 3 different RuleFunctions. toDate is a convenience for sending a DateTime from HTML as a string and when a real DateTime is needed. In reality the event should have the eventTime as a DateTime in the event object but as it has no impact on the example. createObsRes and copyObsRes are created and copied from the Event (to the Concept). The rule for height is perfectly analogous to weight and included herein for completeness as shown in FIG. 11.

Notice that these have the nice property that there is only one Event/Concept in the when clause, so processing these is constant time, O(1). There is still a need to address the issue of whether similar properties can be obtained for every SingletonValue (this will be addressed in a subsequent section), this example is a very common type of Singleton-Value and this will work well in this case. There is still the problem that what is outlined here violates assumption 4. This is addressed in the next Section.

"SingletonValue" and Assumption 4

If the Concept Model is updated every time a new SingletonValue is encountered, the approach in the previous section can be applied. Multiple concepts and linked by IndividualID is not a viable approach. The alternative is change the height and weight fields in Individual from being static "compile time" fields to be dynamic "run time" fields. In one example, an expression in is replaced in the rule condition (when clause) like:
   individual.height_m
with one like:
   getObsRes(individual, "height_m")

An exemplary reasonable solution for this is described in more below. However, it will be appreciated that other solutions may depend on what Rete system is being used.

The approach is to assign a unique integer at run time to each field (specified by a field name string). These numbers start at 0 and go up to $N_f-1$, the number unique dynamic fields that have been seen so far. A simple data structure and rule functions are provided which efficiently find the position for a given field name. Values are stored in an array at the position for its field name. The goal is to come up with two functions (Rule Functions in BE):

1. Concepts.vMR.<type>get<type>(Concepts.Individual individual, String fieldname)
   Gets the value for a field name. Returns null if there is no value.
   Must be useable in "when" clauses of rules.
   Ideally would have worse case amortized complexity of O(1) but $O(\log(N_f))$ is acceptable.
2. void set<type>(Concepts.Individual individual, String fieldname Concepts.vMR.<type> value)
   sets the value for a field name.
   Will never be called from the "when" clause of a rule.
   Ideally would have worse case amortized complexity of O(1) but amortized or expected[3] $O(\log(N_f))$ is acceptable. Worse case may be as bad as $O(N_f)$.

[3] Amortized and expected are two different concepts but either would be acceptable in this case.

A hashtable would be an example. In another embodiment, using a concept for each field name and using Instance.getByExtId(id) and using appropriate @extId (external ids of concepts) to allow O(1) lookup is provided. However, Instance.getByExtId cannot be used in a Rule Function which is used within a rule condition ("when" clause). So this approach is viable for the "set" function, it does not work for the "get" function. It is also possible other Rete systems might support this approach. Below it was not used in the "set" but it can be used to make that function more efficient. However, there will be many "gets" for every "set", so at some level, a different (faster) lookup for "set" might not be worth the programming/maintenance effort. A sorted dynamic (extendable) list of field names is used and a binary search is inherently $O(\log(N_f))$ in worse case.

Figure 12:
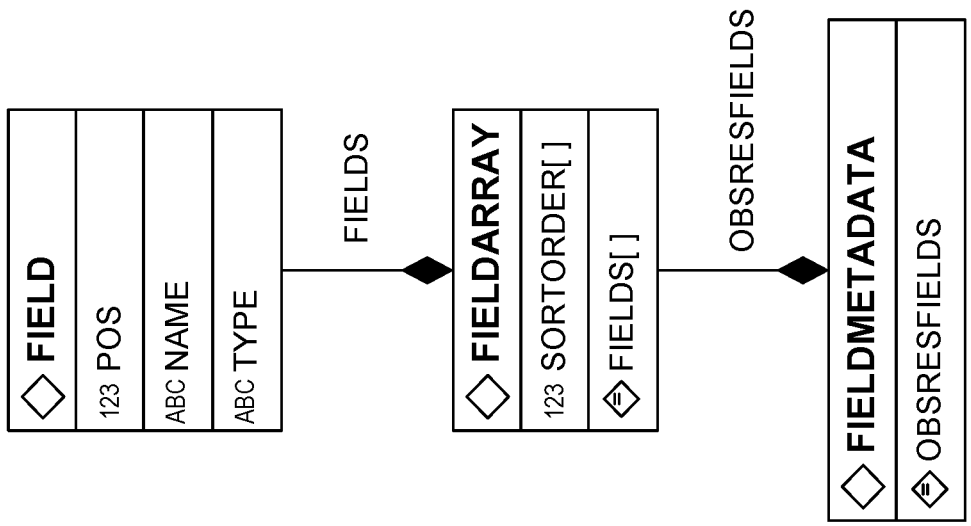
FIG. 12 is a graphical representation of maintaining dynamic fields.

The concepts used for maintaining the dynamics fields are shown in FIG. 12. All fields which are concepts are "ContainedConcept"s which is necessary for them to be accessed in "when" clauses of conditions. The "type" field of Field is not strictly necessary and can be removed or expanded to other meta-data about the Field if desired. Note that Field-MetaData would have one field of type FieldArray for each "type" of Singleton Value it needs to handle. So in the full solution there would be fields for each part of the vMR model being supported. For this example, only one (ObservationResults) is used.

There are two main choices of where to store FieldMetaData. The first choice is in a singleton concept which effectively makes it a global for all individuals. The second choice is to have a local FieldMetaData for each and every individual. In this section the examples are using the first approach. The following chart documents the made tradeoffs of these alternatives. In some instances, the Singleton approach may be more practical (for TIBCO BE, other Rete engines may be different).

Figure 13:
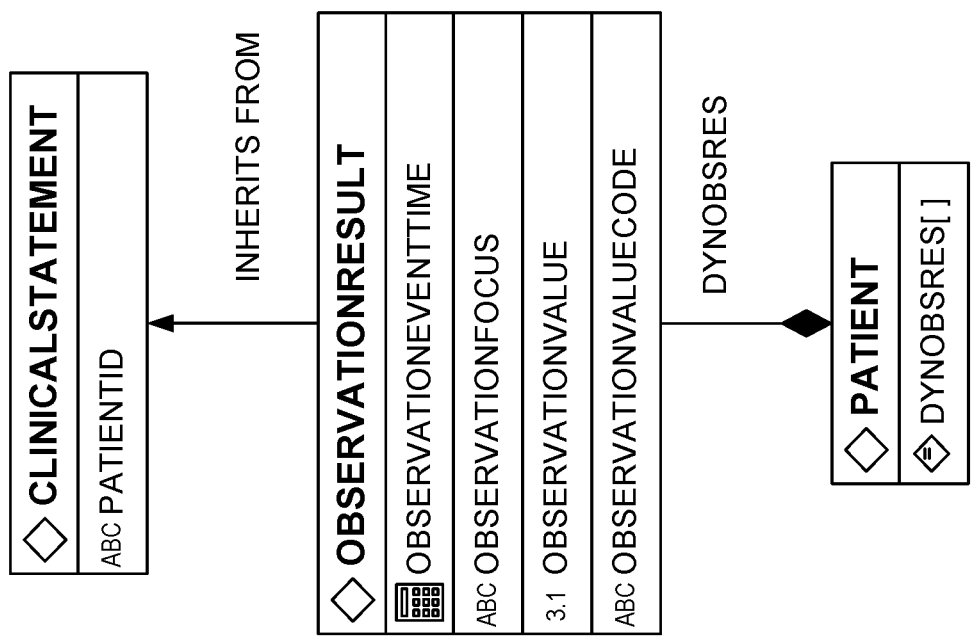
FIG. 13 is a graphical representation of an exemplary design approach.

For each vMR object supported an array of the corresponding Concept is added for that object. So in this example when using ObservationResults would give the following design of FIG. 13.

Given all these concepts, the Rule Functions needed to implement the "get" and "set" method is outlined. A number of functions are used to make this happen. First are the ones which are needed once (the names of these are prefixed with "_") and last are the ones needed once per vMR object type supported.

_lookupFieldPos takes a field name and a sorted list and it finds the element in the list doing a binary search. Its validity is CONDITION as it will be used (indirectly) in the "when" clause of rules. Negative return values are slightly tricky. An example of a negative value is provided in the explanation of _lookupFieldPosDecode shown in FIG. 14. Since the size of the list will be the number of fields, $N_f$. This is a straight forward binary search with a well-known $O(\log(N_f))$ complexity.

lookupFieldPosDecode takes a result returned by _lookupFieldPos and if it was negative converts it to the positive value where it should be located. If I want to add "c", "a,b,d" it should be added at third position which is 2 since the first position is 0. Given that _lookupFieldPos("c", "a,b,d") will return -3 and lookupFieldPosDecode(_lookupFieldPos("c", "a,b,d")) will return 2 as shown in FIG. 15. The total amount of work for this is O(1).

_lookupField takes a field name and a sorted list of fields and returns the field with that field name or null if it is not in the list. Its validity is CONDITION as it will be used (indirectly) in the "when" clause of rules as shown in FIG. 16. The amount of work of this is constant plus one call of _lookupFieldPos so the total work is $O(\log(N_f))$.

_getFieldExtIdPre takes a field name and returns a unique external id for it. The implementation of this is uninteresting and left out. However it is O(1) assuming the max number of characters in a field name is a constant (which I am assuming).

_lookupAndInsertField takes a fieldname, sorted list of fields, and the type of the field in case it needs to create the field. It is the same as _lookupField except it never returns null and will create the field and add it to list of fields if it does not find it. If added to the list, the list will still be sorted after. Modifying concepts in a condition/when clause is not allowed which is why there is both a lookup (for when clauses) and a lookupAndInsert (for actions clauses) as shown in FIG. 17. The actual code in the sample found in section breaks this up into 2 methods (to prevent unnecessary multiple calls to _loopupFieldPos) but is equivalent this this code.

In TIBCO CEP rules, arrays are extendable. If I have an array arr of size Z (arr @length), it has values arr [0] to arr [Z−1]. However if I assign to arr [Z], the array becomes size Z+1. This is utilized in the above code which for people who do not know about this property could be confusing. For the moment, ignore the "for" loop. There is a constant amount of work plus calls (one each) to _lookupFieldPos [$O(\log(N_f))$], _getFieldExtIdPre [O(1)], _lookupFieldPosDecode [O(1)], the "arr[arr@length]= . . . " to extend the array [O(1)]$^4$, and the Field constructor which should also be O(1). This nets out to $O(\log(N_f))$.

The body of the loop is O(1) obviously, so the number of times the loop iterates is key. This is worst case $O(N_f)$ even amortized. However, let $N_s$ be the number of times a "set" function is called with dynamic fields. The "for" loop in a non-amortized sense clearly is executed in the worst case $O(N_f)$. However, in the Singleton FieldMetaData across all "sets" there can be at most $O(N_f^2)$ iterations of the body of the loop. This is because there can only be $N_f$ times a new field can be seen (by definition of $N_f$) and $N_f$ is the worst case for each one of them. So the total cost of is $O(N_s + N_f^2)$ for $N_s$ "sets". If $N_s = \Omega(N_f^2)$ then$^5$ this is $O(N_s)$ for $N_s$ "sets" and amortized O(1). Empirically in my sample implementation, the overhead of this is acceptable. Currently it is estimated that 796 fields can be supported (of all vMR types, 206 max for any one type) and even at 2 orders of magnitude bigger it still reasonable performance. Total is the total time to add all the fields as shown in FIG. 18.

$^5$ O is bounded from above and $\Omega$ is bounded from below.

In the one FieldMetaData for each individual case a field can be new for each individual so you get $O(N_p * N_f^2)$ over all "sets" but $N_f$ is a local (per individual) number of fields not global. It is possible but far from clear that the same O(1) amortized for the "for" loop exists in this case (if $N_s = \Omega (N_p * N_f^2)$ which is feasible in practice but less clear).

The remaining two functions we need once per vMR object type supported and will be used in rules.

getObsResDG takes a individual, a field name, and the singleton FieldMetaData and returns the value of that field for the individual (null if no value stored). The singleton is passed because Instance.getByExtId cannot be called in a rule function useable in "when" conditions of a rule and we need to use this function in the "when" condition as shown in FIG. 19.

As to complexity this is clearly dominated by the call to _lookupField which $O(\log(N_f))$.

setObsResDG takes a individual, a field name, the [new] value and the singleton FieldMetaData. It sets the value of the field. createObsRes is basically a constructor for an ObservationResult from an Event and copyObsRes copies all the fields in the Event version of the vMR object to the Concept version of the vMR object. The implementations are straight forward and omitted here but are O(1) as shown in FIG. 20. The code in the sample project is equivalent to this but it has been split into 2 functions so prevent unnecessary additional (indirect) calls to _lookupField.

The cost of this is dominated by the cost of the call to _lookupAndInsertField call and is $O(N_f)$ but expected $O(\log(N_f))$.

The rule is a straightforward modification of the rules with static fields. For example, one point to call out is the Concepts.DynFields.FieldMetaDatafmd_singleton;
in the "declare". However, even though there are 2 things in the "declare" resulting in a cross product. However, since there is only one FieldMetaData there is no combinatorics concern. As written here, there is a problem with every rule having to be reconsidered if the fmd_singleton element changes (which it will when a new field is assigned) as shown in FIG. 21. This problem will be addressed later in this analysis. The table in FIGS. 22 and 23 summarize all the complexities in this section.

Using Function Calls in Conditions

BE tries to be efficient in determining which rules need to be considered for addition to the agenda. It operates by a rule that if "nothing has changed" in the data used in the rule condition (when clause of the rule), then the rule doesn't even need to be considered. So for the following simple (and not realistic example because no null check is used) of FIG. 24, if anything for the individual changes except p.weight_kg.observationValue the rule is not considered for agenda creation. However if p.weight_kg.observationValue does change the rule is considered.

```
declare {
    Concepts.Individual p;
}
when {
    p.weight_kg.observationValue >= 100;
}
then {...}
```

In FIG. 25, if we replace the static field with a dynamic field and a function call:

```
declare {
    Concepts.Individual p;
    Concepts.DynFields.FieldMetaData fmd_singleton;
}
when {
    getObsResDG(p, "weight_kg",fmd_singleton) >= 100;
}
then {...}
```

In this case since the function is treated as opaque it is assumed if any part of p changes this rule will be considered for agenda creation. This can be mitigated some by instead of passing p into getObsResDG, we pass p.dynObsRes instead[6]. This will restrict consideration for agenda creation to when any dynamic field stored in dynObsRes changes but if other parts of p changes, it won't be considered. However, the bigger concern is when fmd_singleton changes. When it does than every rule for every individual needs to be reconsidered. This would be prohibitively expensive. However it is also completely unnecessary since changes to fmd_singleton cannot change the evaluated result of any rule condition (when) unless a dynamic field in a individual was also changed (a change to fmd_singleton means a new field never seen before was just seen, but since it was never seen, no value for it can be stored in any individual yet). So with clever use of "forwardChain=false", this cost can be avoided.

[6] Passing p. dynObsRes directly will give a compile time error but it is possible to pass it by creatively wrapping it in a concept.

Figure 26:
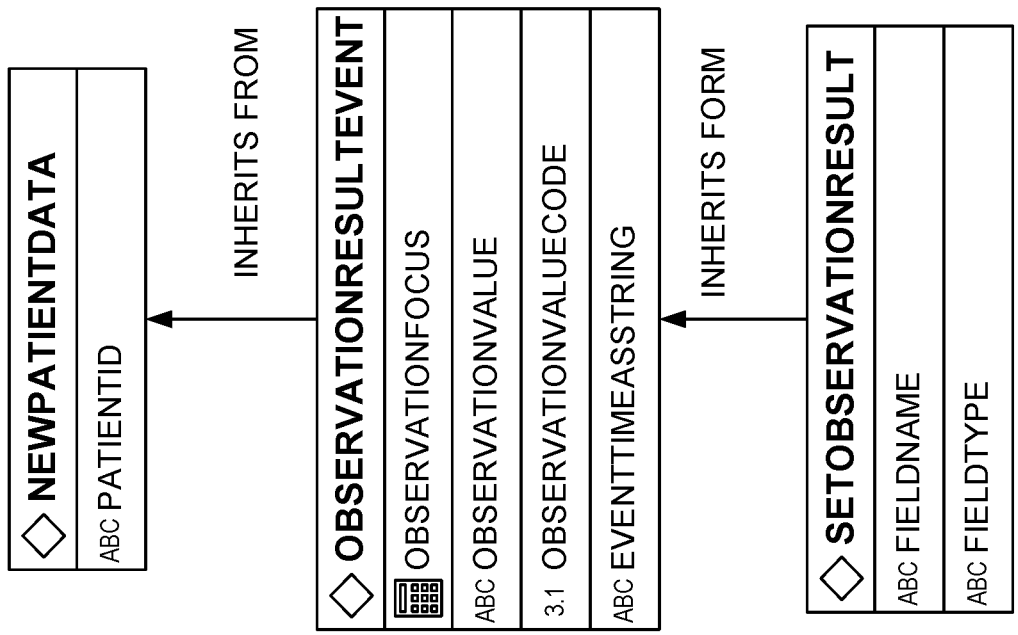
FIG. 26 is a graphical representation of an exemplary extended event model.

This is done by replacing not directly using the "set" function for dynamic fields (e.g., setObsResDG) but instead assert a new event to do the set. The Event model needs to be extended to have SetObservationResult inherit from ObservationResultEvent as shown in FIG. 26.

In FIG. 27, the dynamic version of the BodyWeightKG rule using the set is[7]:

[7] In the code in the sample project, the then is replaced by a function call which does the same thing so that we don't have to duplicate the same code for each rule. It requires creating one function for each SingletonValue function/vMR object type pair supported. In the sample code this is MostRecentlObservationResult. The version in the sample code also has some additional code for gathering empirical data.

In FIG. 28, we replace the

```
setObsResDG(individual,fieldName,orEvent,fmd_singleton);
```

With of FIG. 29

```
Events.SetObservationResult setEvent =Event.createEvent
    ("[magic string]");
Event.assertEvent(setEvent);
```

Figure 30:
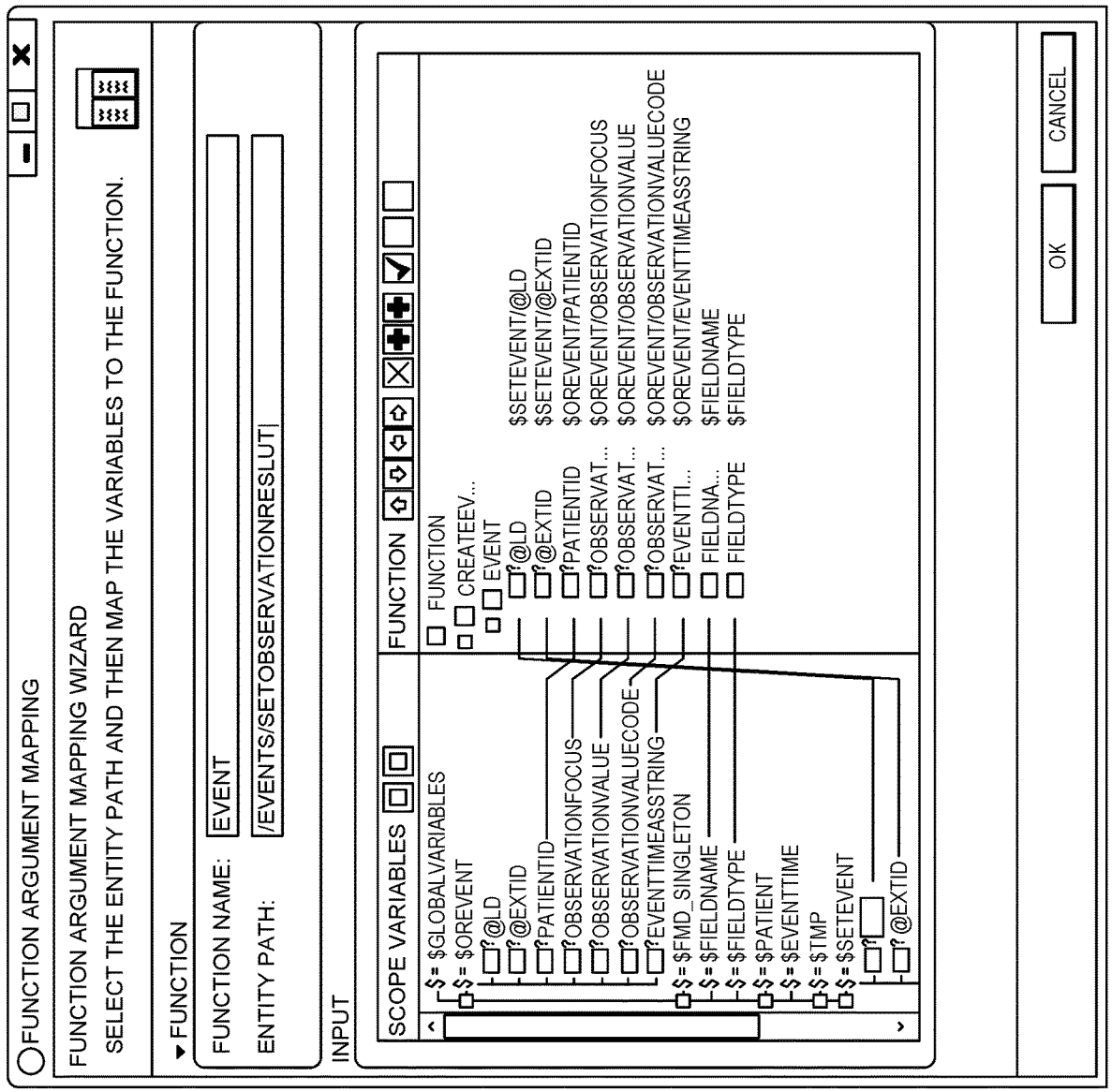
FIG. 30 is a graphical representation of mapping values.

The magic string is not useful. In BE if you mouse over the real string, hold the <CTRL> button and click the left mouse button you open the editor which shows how to create the new event. The mapping of values captured in [magic string] is[8] shown in FIG. 30.

[8] Mapping in the sample project is slightly more complicated but only for optimization and debugging.

Now to get the right behavior, two rules are created (priority is very relevant). Referring to FIG. 31, The first one has forward chaining off (so that if the singleton FieldMetaData changes all rules using it will not be re-evaluated).

Basically all it does is add the field to FieldMetaData if it is not already there (it does not set the value for the individual).

The second method has forward chaining on and it just sets the value for the individual (but since it has a lower priority FieldMetaData will not be updated by this method). Forward chaining on is desirable because we do want to reconsider rules that rely on this dynamic fields value as shown in FIG. 32.

Note: Consuming the event is critical. Otherwise the rule that created this event will fire off the SetObservationResult event and loop forever. This is dangerous. Using a more complex event model (change the inheritance) can eliminate this potential infinite chain of events (if someone removed the consumeEvent or changes the priorities incorrectly).

NOTE: This version of setting calls _lookupFieldPos up to 3 times from:
  Rules.DynFieldsGlob.DG_BodyWeightKG
    calls getObsResDG calls _lookupField calls _lookupFieldPos
    Potentially asserts an Events.SetObservationResult which triggers
      Rules.DynFieldsGlob.DG_UpdateFieldsObsRes
        calls _lookupAndInsertField calls _lookupFieldPos
      Rules.DynFieldsGlob.DG_SetValueObsRes calls setObsResDG calls _lookupAndInsertField calls _lookupFieldPos It is possible to rewrite the code to save the position from the first call in the Events.SetObservationResult event so that the other two calls can be eliminated. The code in the example does this.

Empirically, by averaging runs of repeatedly setting the same fields over and over again 100,000 times on the same individual, static fields sets take .053 ms, dynamic fields with direct function calls to set take 0.067 ms (28% longer), and using the set event method takes 0.106 ms (twice as long as static fields and 58% longer than direct calls). Having 2 dynamic fields verse having 2,000 makes very little difference (2 k look 4.6% longer)

In another embodiment, the cost of adding a never before seen dynamic field when there are already existing individuals is examined. Runs of this are more difficult so I did not do repeated runs to average times (hence nothing is less than 1 MS) plus there are constant overheads in the timing (same if do one or a million) that get spread out over with multiple runs. So don't react no 1 ms verse 0.053 ms above for static fields as shown in FIG. 33. For static field and dynamic with set event, slow growth may be affected by underlying memory management.

Dynamic Field Approach

Static fields have less overhead and capture "what changed" more accurately for determining which expressions in when clauses to re-evaluate. However, adding new static fields requires bringing down the system and updating the data structures. In one embodiment, a hybrid approach should be used. For Singleton Value that are "hot spots" we should use a static field but for non "hot spot" Singleton Value or new ones we did not anticipate, we use dynamic fields. I am leaving "hot spot" vague but in spirit it is any Singleton Value which triggers a significant amount of processing (including evaluation in rule conditions (when clauses)). However, we could do the same for any Singleton Value that we anticipate if appropriate (even if it is not a hot spot).

Additionally, in an example using one dynamic structure per type, there is M per type with hash a name string into which of the M to use for that name (e.g., for a naïve model, if the ASCII code of the last character is even then use structure 1, if odd then use structure 2). This will allow BE to more exclude more rules from consideration without re-evaluating their when clauses.

Covering Full Range of Possible SingletonValue

SingletonValue could effectively be expressed a query against vMR that returns a sequence a particular vMR object type (e.g., ObservationResult) based on a condition (limited semantics, for example "or" is not possible). A function is applied to that sequence to ensure that the end result is either a single number or 1 object from that sequence. The question is how to handle any possible SingletonValue with rules. Starting conceptually, embodiments of the present invention handle when a vMR object would "newly meet" the criteria of an Singleton Value. "Newly meet" means either the vMR object didn't exist before or it did but previously the condition for the SingletonValue evaluated to false but now it evaluates to true. Embodiments of the present invention also handle the case when a vMR object would "newly not meet" the criteria of an Singleton Value. "Newly not meet", means the vMR object existed before and the condition for the SingletonValue evaluated to true on it, however now it evaluates to false.

Embodiments of the present invention handle any Singleton Value is to a) recognize when an object "newly meets" or "newly does not meet" the criteria for an SingletonValue and b) for each function how to update the value of the SingletonValue given the "new" information.

There are three reasons an existing vMR object could "newly meet" or "newly not meet" the condition for an Singleton Value.
1. Passage of time. The condition could, for example, have time component (e.g., in the last week) which can change the evaluation as time progresses.
   In this case, either Time Events, Schedule Simple Events or something equivalent outside of BE are used. When you first process a vMR object, if at a certain time it would disqualify (or possibly qualify but that is less common) you need to make sure at that time an event will get triggered which can then update the SingletonValue value appropriately at that time.
2. The data for the vMR object itself could be updated. This is not (for example) a new weight Observation Result but would be amending an existing weight observation result (e.g., because there was a typing error when it originally was created). In practice changing data should be an exception probably should be handled through a special case.
   The case of going from "does not meet" to "meets" is the base situation that has been handled throughout this document and doesn't need anything special to address it. If the other direction is relevant, effectively you can have a rule which is the negation of the condition for the SingletonValue and a way to know if the vMR data is new or updated. It may also be helpful to know the "before update" value of the condition.
3. An update to the conditions of a rule (e.g., the rule is updated).
   One embodiment is to reevaluate that SingletonValue for all individuals.

As for how to compute the functions, one way is to do a query to get the entire sequence and apply the function to that sequence. This is a viable approach in some cases. However, other approaches may be available that do not require a full query. In all of the following let the objects in the sequence be of type vMRType, "p" be the Concept for the relevant individual and "vo" be the Event or Concept for the vMR object being processed as shown in FIG. 34.

mostrecent(dt) where dt is a datetime field within vMRType
  description: return object in the sequence with the most recent datetime in dt
  stores: edVal vMRType. Which is the most recent one (null if none)
  how: how to compute without getting full sequence

```
"newly meets"
if (p.edVal == null || (p.edVal.dt < vo.dt) {
  p.edVal = vo;
}
If one processing is more recent then use the one processing.
"newly not meets": 1. Passage of Time
if (p.edVal == vo) {
  p.edVal = null;
}
This works under the assumption that there is one time
window with no gaps when objects qualify
for inclusion in the sequence. In that case, if this was the
most recent but it no longer qualifies because it no longer
falls into the time window, we can't know of a more
recent one that does (as that contradicts that this is the
most recent).
"newly not meets": 2. Data Change
Query to get full sequence and compute.
The only other approach is to maintain the while sequence
in "p", but I would rather just query in that case.
``` min(v) where v is a value field within vMRType as shown in FIG. 35
  description: return object in the sequence with the smallest value in v
  stores: edVal vMRType. Which is the min one (null if none)
  how: how to compute without getting full sequence

```
"newly meets"
if (p.edVal == null || ( (p.edVal.v > vo.v) {
  p.edVal --= vo;
}
If one processing is smaller, store it
"newly not meets": 1. Passage of Time
Query to get full sequence and compute.
The only other approach is to maintain the while sequence
in "p", but I would rather just query in that case.
"newly not meets": 2. Data Change
Query to get full sequence and compute.
The only other approach is to maintain the while sequence
in "p", but I would rather just query in that case.
``` max(v) where v is a value field within vMRType as shown in FIG. 36
  description: return object in the sequence with the largest value in v
  stores: edVal vMRType. Which is the max one (null if none)
  how: how to compute without getting full sequence

```
"newly meets"
if (p.edVal == null || (p.edVal.v < vo.v) {
  p.edVal = vo;
}
If one processing is smaller, store it
"newly not meets": 1. Passage of Time
Query to get full sequence and compute.
The only other approach is to maintain the while sequence
``` in "p", but I would rather just query in that case.
"newly not meets": 2. Data Change
Query to get full sequence and compute.
The only other approach is to maintain the while sequence in "p", but I would rather just query in that case.

--- count(v) where v is a value field within vMRType (ignored) as shown in FIG. 37
description: return the number of objects in the sequence
stores: edVal int.
how: how to compute without getting full sequence

---

"newly meets"
p.edVal++;
One more than before.
"newly not meets": 1. Passage of Time
p.edVal--;
One less than before.
"newly not meets": 2. Data Change
p.edVal--;
One less than before.

--- average(v) where v is a value field within vMRType as shown in FIG. 38
description: return the average of v over objects in the sequence
stores: edVal {count: int; total: double}.
how: how to compute without getting full sequence

---

"newly meets"
p.edVal.count++; p.edVal.total+=vo.v;
The average is obviously p.edVal.total/p.edVal.count
"newly not meets": 1. Passage of Time
p.edVal.count--; p.edVal.total-= vo.v;
The average is obviously p.edVal.total/p.edVal.count
"newly not meets": 2. Data Change
p.edVal.count--; p.edVal.total-= prev(vo.v);
The average is obviously p.edVal.total/p.edVal.count
prev(vo.v) is the before change value of vo.v. If that is not known then will need to query to get full sequence and compute.

--- previous(dt) where dt is a datetime field within vMRType as shown in FIG. 39
description: return object in the sequence with the second most recent datetime in dt
stores: edVal {mostRecent: vMRType; previous vMRType}. Which is the most recent one (null if none)
how: how to compute without getting full sequence

---

```
"newly meets"
if (p.edVal.mostRecent == null) {
    p.edVal.mostRecent = vo;
} else {
    if (p.edVal.mostRecent.dt < vo.dt) {
        p.edVal.previous = p.edVal.mostRecent;
        p.edVal.mostRecent = vo;
    } else {
        if (p.edVal.previous == null || p.edVal.previous.dt < vo.dt) {
            p.edVal.previous = vo;
        }
    }
}
```
If one processing is more recent then use the one processing.
"newly not meets": 1. Passage of Time
```
if (p.edVal.mostRecent == vo) {
    p.edVal.mostRecent = null;
    p.edVal.previous =null; // C1
} else if (p.edVal.previous == vo) {
    p.edVal.previous = null;
}
```
This works under the assumption that there is one time window with no gaps when objects qualify for inclusion in the sequence. In that case, if this was the most recent but it no longer qualifies because it no longer falls into the time window, we can't know of a more recent one that does (as that contradicts that this is the most recent).
The assignment with the comment "C1" makes sense because if the most recent is too old the second most recent is also too old and in the rare situation they have the same (or almost same) timestamp, we cannot be sure which one will be processed first, so there is some chance it is not null already.
"newly not meets": 2. Data Change
Query to get full sequence and compute.
The only other approach is to maintain the while sequence in "p", but I would rather just query in that case.

last(dt) where dt is a datetime field within vMRType as shown in FIG. 40 description: return object in the sequence with the oldest datetime in dt stores: edVal vMRType). Which is the oldest one (null if none)

how: how to compute without getting full sequence

```
"newly meets"
if (p.edVal == null) {
    || (p.edVal.dt > vo.dt) {
    (p.edVal = vo;
}
If one processing is more recent then use the one processing.
"newly not meets": 1. Passage of Time
Query to get full sequence and compute.
The only other approach is to maintain the while sequence
in "p", but I would rather just query in that case.
"newly not meets": 2. Data Change
Query to get full sequence and compute.
The only other approach is to maintain the while sequence
in "p", but I would rather just query in that case.
```

As shown in FIG. 41,

| | |
|---|---|
| Content Translator | Content Translator: In this model content in one form (currently as XML files) is automatically converted into Pluggable Content as defined above. This can also be generalized into a content IDE (Integrated Development Environment). Generalized Analogy: XCode IDE, Android Eclipse IDE/SDK. |
| Core Product | Core Product: may include CareXcell or Healthe Care but does not include the content itself. Analogy: Smart Phone. |
| $N_c$ | Number of Concepts used in the rule (in the declare) |
| $N_f$ | The number of unique dynamic fields that exist. |
| $N_g$ | Number of times a "get" function is called with dynamic fields. |
| $N_p$ | Number of Individuals |
| $N_s$ | Number of times a "set" function is called with dynamic fields. |
| Individual Data Model | Individual Data Model: The data model for individual medical data assumed by the content. |
| Pluggable Content | Pluggable Content: This is the functionality related to a disease or other clinically interesting concept. It is released independently of the Core Product but can also require particular versions (possibly one version) of the Core Product to work. Analogy: Smartphone App |
| Rete Data Model | Rete Data Model: The data model for individual data used in the rules/Rete network. In general this may or may not be the same as the Individual Medical Data Model. In CEP, such as TIBCO BE, this manifests as "Concepts" or "Events". |

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computer-implemented system for creating extensible data structures for rule based systems to improve complex event processing, the computer-implemented system comprising:

a processor; and a non-transitory computer storage medium storing computer-usable instructions that, when used by the processor, cause the processor to:

access, at a core product, an underlying individual data model containing medical content;

automatically translate, at a content translator, the content from the underlying individual data into pluggable content that is functionally related to a disease or medically interesting concept, the pluggable content released independently of the core product and not requiring updates to the core product or the content translator, the pluggable content comprising singleton values, wherein a singleton value of the singleton values comprises a static field when the singleton value is a hot spot or a dynamic field when the singleton value is not a hot spot, the hot spot indicating the singleton value triggers a threshold amount of processing or an evaluation in rule conditions;

utilize the singleton values for rules in a rete model; and utilize the results of execution of the rules of the rete model in a complex event processing system to improve the execution of the complex event processing system.

2. The system of claim 1, wherein the individual data model is one of HL7 vMR or FHIR.

3. The system of claim 1, wherein the singleton values represent no value or a single value.

4. The system of claim 1, wherein the rete model is utilized for pattern matching.

5. The system of claim 4, utilizing the pattern matching to identify meaningful events from the singleton values derived for multiple individual data models.

6. The system of claim 1, further comprising:

determining if the singleton value newly meets or does not newly meet criteria for being processed by the rete model.

7. The system of claim 1, wherein a content translator translating xml content from the underlying individual data model into pluggable content that is functionally related to a disease or medically interesting concept.

8. The system of claim 1, wherein the translation is performed as batch processing of individual data models containing medical content.

9. The system of claim 1, wherein the translation is event based processing of multiple individual data models containing medical content.

10. One or more non-transitory computer storage media having computer-usable instructions that, when used by one or more computing devices, cause the one or more computing devices to perform a method creating extensible data structures for rule based systems to improve complex event processing, the method comprising:

accessing, at a core product, an underlying individual data model containing medical content;

automatically translating, at a content translator, the content from the underlying individual data model into pluggable content that is functionally related to a disease or medically interesting concept, the pluggable content released independently of the core product and not requiring updates to the core product or the content translator, the pluggable content comprising singleton values, wherein a singleton value of the singleton values comprises a static field when the singleton value is a hot spot or a dynamic field when the singleton value is not a hot spot, the hot spot indicating the singleton value triggers a threshold amount of processing or an evaluation in rule conditions;

utilizing the singleton values for rules in a rete model; and utilizing the results of execution of the rules of the rete model in a complex event processing system to improve the execution of the complex event processing system.

11. The media of claim 10, wherein the individual data model is one of HL7 vMR or FHIR.

12. The media of claim 10, wherein the singleton values represent no value or a single value.

13. The media of claim 10, wherein the rete model is utilized for pattern matching.

14. The media of claim 13, utilizing the pattern matching to identify meaningful events from the singleton values derived for multiple individual data models.

15. The media of claim 10, further comprising:

determining if the singleton value newly meets or does not newly meet the criteria for being processed by the rete model.

16. The media of claim 10, wherein a content translator translating the xml content from the underlying individual data model into pluggable content that is functionally related to a disease or medically interesting concept.

17. The media of claim 10, wherein the translation is performed as batch processing of individual data models containing medical content.

18. The media of claim 1, wherein the translation is event based processing of multiple individual data models containing medical content.

* * * * *

UNITED STATES PATENT AND TRADEMARK OFFICE
CERTIFICATE OF CORRECTION

| | | |
|---|---|---|
| PATENT NO. | : 11,062,221 B1 | Page 1 of 2 |
| APPLICATION NO. | : 15/187321 | |
| DATED | : July 13, 2021 | |
| INVENTOR(S) | : Landi et al. | |

It is certified that error appears in the above-identified patent and that said Letters Patent is hereby corrected as shown below:

On the Title Page

• Item (57), Column 2, Line 7: In Abstract, delete "fo" and insert -- of --, therefor.

In the Drawings

• Sheet 10 of 44 (FIG. 10.), Line 1: Delete "evenTime)" and insert -- eventTime) --, therefor.
• Sheet 23 of 44 (FIG. 21.), Line 13: Delete "weightkg"," and insert -- "weight_kg", --, therefor.
• Sheet 35 of 44 (FIG. 33.), Line 1: Delete "PATINETS" and insert -- PATIENTS --, therefor.
• Sheet 37 of 44 (FIG. 35.), Line 14: Delete "FIG.35." and insert -- FIG. 35. --, therefor.
• Sheet 42 of 44 (FIG. 39.), Line 10: Delete "firet," and insert -- first, --, therefor.
• Sheet 43 of 44 (FIG. 40.), Line 6: Delete "thne" and insert -- then --, therefor.

In the Specification

• Column 1, Line 41, Delete "0(1);" and insert -- O(1); --, therefor.
• Column 3, Line 6, Delete "Electronic" and insert -- Electronics --, therefor.
• Column 6, Line 5, delete "phIndividualId;" and insert -- ph.IndividualId; --, therefor.
• Column 8, Line 42-43, Delete ""ContainedConcept"s" and insert -- "ContainedConcepts" --, therefor.
• Column 9, Line 13, delete "lookupFieldPosDecode" and insert -- _lookupFieldPosDecode --, therefor.
• Column 9, Line 18, delete "return-3" and insert -- return -3 --, therefor.
• Column 9, Line 18, delete "lookupFieldPosDecode" and insert -- _lookupFieldPosDecode --, therefor.
• Column 9, Line 42, delete " _loopupFieldPos)" and insert -- _lookupFieldPos) --, therefor.
• Column 10, Line 34, delete " _lookupAndInsertField" and insert -- _lookupAndInsertField --, therefor.
• Column 11, Line 32, delete "p. dynObsRes" and insert -- p.dynObsRes --, therefor.
• Column 11, Line 43-44, delete "MostRecentlObservationResult." and insert Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,062,221 B1

-- MostRecent/ObservationResult. --, therefor.
- Column 11, Line 65, delete "The" and insert -- the --, therefor.
- Column 12, Line 26, delete "_lookupAndInsertField" and insert -- _lookupAndInsertField --, therefor.
- Column 12, Line 34, delete "take.053 ms," and insert -- take 0.053 ms, --, therefor.
- Column 12, Line 39, delete "longer)" and insert -- longer). --, therefor.
- Column 17-18, Line 31, delete "declare)" and insert -- declare). --, therefor.
- Column 17-18, Line 34, delete "Individuals" and insert -- Individuals. --, therefor.